United States Patent
Chelli et al.

(10) Patent No.: US 11,626,699 B2
(45) Date of Patent: *Apr. 11, 2023

(54) FLUID CONNECTOR

(71) Applicant: Bellco S.R.L., Mirandola (IT)

(72) Inventors: Niccolo Chelli, Rufina (IT); Giuliano Giganti, Oppido Lucano (IT)

(73) Assignee: Bellco S.R.L., Mirandola (IT)

( * ) Notice: Subject to any disclaimer, the term of this patent is extended or adjusted under 35 U.S.C. 154(b) by 21 days.

This patent is subject to a terminal disclaimer.

(21) Appl. No.: 17/191,395

(22) Filed: Mar. 3, 2021

(65) Prior Publication Data

US 2022/0285893 A1 Sep. 8, 2022

(51) Int. Cl.
*H01R 24/28* (2011.01)
*H01R 13/62* (2006.01)

(52) U.S. Cl.
CPC ............ *H01R 24/28* (2013.01); *H01R 13/62* (2013.01)

(58) Field of Classification Search
CPC .... H01R 24/28; H01R 13/62; H01R 13/6205; H01R 13/7035; H01R 13/7028; H01R 13/701; H01R 13/71; H01R 13/44; H01R 13/658; H01R 12/30; H01R 11/30
USPC ....................................................... 439/136
See application file for complete search history.

(56) References Cited

U.S. PATENT DOCUMENTS

| | | | | | |
|---|---|---|---|---|---|
| 3,115,116 | A | * | 12/1963 | Lorell | A01J 5/017 |
| | | | | | 119/14.08 |
| 3,878,819 | A | * | 4/1975 | Harman | A01J 5/017 |
| | | | | | 119/14.08 |
| 5,896,827 | A | * | 4/1999 | Brown | A01J 5/007 |
| | | | | | 119/14.37 |
| 6,920,840 | B1 | * | 7/2005 | Sloan | A01J 5/08 |
| | | | | | 119/14.47 |
| 8,978,584 | B2 | * | 3/2015 | Uslar Valenzuela | A01J 5/007 |
| | | | | | 119/14.08 |
| 2017/0281847 | A1 | * | 10/2017 | Manda | A61K 33/00 |

OTHER PUBLICATIONS

U.S. Appl. No. 17/195,256, filed Mar. 8, 2021, naming inventors Chelli et al.

* cited by examiner

*Primary Examiner* — Harshad C Patel
(74) *Attorney, Agent, or Firm* — Shumaker & Sieffert, P.A.

(57) ABSTRACT

In some examples, a connector includes a plug configured to mechanically couple with a socket to establish fluid communication from a first conduit to a second conduit. The plug is configured to mechanically engage the first conduit and the socket is configured to mechanically engage the second conduit. In examples, the plug is configured to insert into a socket well of the socket. The connector includes a clamp head configured to mechanically engage the plug when the plug mechanically couples with the socket. The clamp head is configured to mechanically engage the plug to help sustain the mechanical coupling of the plug and the socket. In some examples, the connector may include an output device configured to provide an output indicating when the plug is mechanically coupled with the socket.

20 Claims, 7 Drawing Sheets

FLUID CONNECTOR

TECHNICAL FIELD

This disclosure is related to a fluid system connector.

BACKGROUND

Dialysis machines may be used to remove waste products from blood of a patient when the kidneys of the patient are no longer able to adequately do so. During dialysis, the dialysis machine may generate or regenerate dialysate using specified concentrations of solute buffers, osmotic agents, cations, and other concentrates for biocompatibility with the patient. The dialysis machine may provide the dialysate to a cycler for delivery to the patient. The generation or regeneration of dialysate may require a patient or another user to perform physical connections between external (e.g., disposable) elements and the dialysis machine.

SUMMARY

This disclosure describes a connector configured to establish a connection between a container configured to store a material, such as a medical solution in fluid form, solid form, or any other suitable form, and a machine line of a medical machine configured to utilize the material to provide therapy to a patient. The connector is configured to establish the connection through the mechanical mating of a plug and a socket. The plug is configured to mechanically engage the container and the socket is configured to mechanically engage the machine line. In examples, the plug is configured to insert into a socket well defined by the socket to provide the mechanical mating. The connector includes a clamp head configured to mechanically engage the plug when the plug mechanically couples with the socket, in order to assist in maintaining the plug mechanically mated with the socket.

In an example, a connector comprises: a plug defining a fluid channel extending between a plug inlet defined by the plug and a plug outlet defined by the plug, wherein the plug inlet is configured to mechanically engage a first conduit; a socket including a clamp head, wherein the socket is configured to mechanically engage a second conduit, and wherein the plug is configured to mechanically couple with the socket to fluidly couple the first conduit and the second conduit; an actuator configured to translate the clamp head to cause the clamp head to mechanically engage the plug when the actuator receives electrical power; and a control circuit configured to provide the electrical power to the actuator, wherein the plug is configured to cause the control circuit to provide the electrical power to the actuator when the plug mechanically couples with the socket, and wherein the clamp head is configured to help sustain the mechanical coupling of the plug and the socket when the clamp head mechanically engages the plug.

In an example, a connector comprises: a plug defining a fluid channel extending between a plug inlet defined by the plug and a plug outlet defined by the plug, wherein the plug inlet is configured to mechanically engage a first conduit; a socket including a first clamp head and a second clamp head, wherein the socket is configured to mechanically engage a second conduit, and wherein the plug is configured to mechanically couple with the socket to fluidly couple the first conduit and the second conduit, wherein the first clamp head is configured to exert a first force on the plug when the plug mechanically couples with the socket, wherein the second clamp head is configured to exert a second force on the plug when the plug mechanically couples with the socket, wherein the second force opposes the first force, and wherein the first clamp head is configured to exert the first force and the second clamp head is configured to exert the second force to help sustain the mechanical coupling of the plug and the socket; an actuator configured to receive electrical power, wherein the actuator is configured to translate the first clamp head to cause the first clamp head to exert the first force on the plug and configured to translate the second clamp head to exert the second force on the plug when the actuator receives the electrical power; and a control circuit configured to provide the electrical power to the actuator, wherein the plug is configured to cause the control circuit to provide the electrical power to the actuator when the plug mechanically couples with the socket.

In an example, a method comprises: mechanically coupling a plug and a socket, wherein the plug defines a plug inlet, a plug outlet, and a fluid channel extending between the plug inlet and the plug outlet, wherein the plug inlet is configured to mechanically engage a first conduit, and wherein the socket is configured to mechanically engage a second conduit, wherein when the plug mechanically couples with the socket, a control circuit provides electrical power to an actuator configured to translate a clamp head to mechanically engage the plug to help sustain the mechanical coupling of the plug and the socket; and, subsequently, decoupling the plug and the socket.

The details of one or more examples are set forth in the accompanying drawings and the description below. Other features, objects, and advantages will be apparent from the description and drawings, and from the claims.

DETAILED DESCRIPTION

Figure 1:
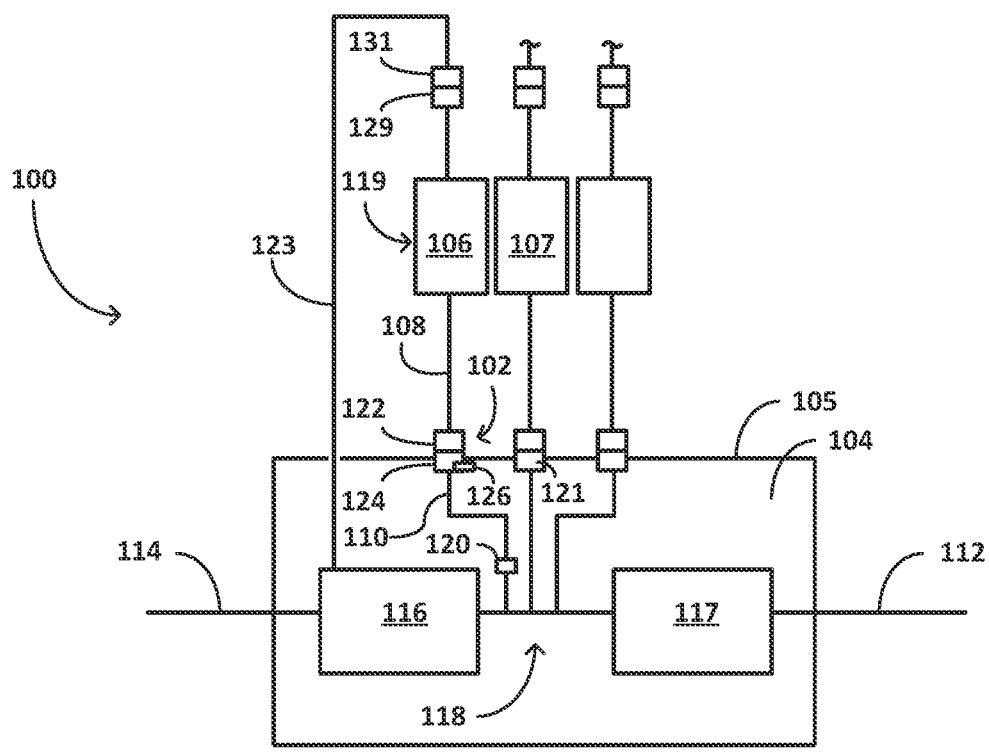
FIG. 1 is a conceptual diagram illustrating an example medical system configured to deliver a medical fluid such as dialysate.

This disclosure describes a connector configured to establish a connection between a medical machine and a container that stores material for use by the medical machine in a medical treatment of a patient. In some examples, the connector is configured to provide a connection between a materials source, such as a medical container (e.g., a bag) holding a medical material (e.g., in a solid and/or a liquid state), and a medical machine configured to utilize the medical material to provide therapy to a patient. The connector includes a plug configured to mechanically couple with a socket to provide the connection. For example, the connector may be configured such that the plug inserts into the socket (e.g., by the patient, a patient caretaker, or a clinician) to mechanically couple with the socket. The connector includes an actuator configured to cause a clamp head to mechanically engage the plug when the plug mechanically couples with the socket, in order to help sustain the mechanically coupling and prevent inadvertent disconnection of the container and the medical machine. In examples, the connector provides a fluid connection between a container containing a concentrate solution and a dialysis machine configured to utilize the concentrate solution to deliver dialysate to the patient.

The connector may be configured to substantially ensure a stable connection in systems involving pharmacological preparation and delivery to a patient. For example, the connector may be advantageous when a procedure requires the patient or another user (e.g., a patient caretaker or clinician) to make a physical connections between a container, such as a disposable concentrate bag, and a medical machine, such as a dialysis machine. For example, the connector may be utilized to provide a positive indication to the patient or other user that the physical connection has been established. The connector may be configured to substantially minimize or prevent inadvertent disconnections between the container and medical machine during medical treatment and/or production of a medication or other therapeutic material to provide therapy to a patient. In some examples, the connector is configured to be used with a medical machine to provide an indication to the patient or other user that the physical connection has been lost, signaling that the medical treatment and/or production of the medication is no longer occurring as intended. The connector may have particular advantages when utilized in home therapy delivery systems such as home dialysis systems where the patient or an assisting user may be required to satisfactorily perform and maintain physical connections between one or more containers and the home therapy delivery system.

The plug of the connector is configured to mechanically engage a first conduit such as a container tube connected to a container. The plug is configured to mechanically engage the first conduit to connect the first conduit and a plug inlet defined by the plug. The plug defines a fluid channel ("plug channel") extending from the plug inlet to a plug outlet defined by the plug. The plug is configured such that, when the plug mechanically engages the first conduit, the plug establishes a flow path for a fluid (e.g., a medical material) from a lumen of the first conduit, through the fluid passage, and to the plug outlet.

The socket of the connector is configured to mechanically engage a second conduit, such as a line (e.g., a fluid line) within a medical machine ("machine line"). The socket is configured to mechanically engage the second conduit to connect the plug outlet and the second conduit. The socket is configured such that, when the plug mechanically couples with the socket, the connector establishes a flow path from a lumen of the first conduit mechanically engaged by the plug to a lumen of the second fluid line mechanically engaged by the socket. In some examples, a housing of a medical machine (e.g., a dialysis machine) mechanically supports the socket and the machine line. For example, the socket may be affixed to or an integral part of the housing, and the machine line may be affixed to or an integral part of the socket and/or housing. Hence, the connector may be configured such that a user (e.g., a patient, patient caretaker, or clinician) may translate the plug toward the socket to mechanically couple the plug and socket and fluidically couple a first conduit (e.g., tubing for a container) and a second conduit (e.g., a machine line within a medical machine), such that the medical machine may utilize a medical material within the container to provide therapy to the patient.

The socket includes a clamp head configured to mechanically engage the plug when the plug mechanically couples with the socket. The clamp head may be configured to minimize movements of the plug which might tend to cause an uncoupling of the plug and the socket. In examples, the plug is configured to mechanically couple with the socket in a first direction, and the clamp head is configured to mechanically engage the plug to resist translation of the plug in a second direction opposite the first direction. In some examples, the plug is configured to insert into a socket well defined by the socket to mechanically couple with the socket, and the clamp head is configured to retain the plug within the socket well. The connector is configured to maintain the connection between the first conduit mechanically engaged by the plug and the second conduit mechanically engaged by the socket using the clamp head.

The plug may be configured to cause a control circuit to provide electrical power to an actuator when the plug mechanically couples with the socket. The actuator may be configured to translate the clamp head to cause the clamp head to mechanically engage the plug. Hence, the connector may be configured such that the mechanical coupling of plug and the socket causes the plug to actuate the control circuit to provide the electrical power to the actuator, and in response to receiving the electrical power, the actuator translates the clamp head to mechanically engage the plug. For example, the plug may be configured to cause the control circuit to provide the electrical power to the actuator when the plug inserts into a socket well defined by the socket, such that the clamp head mechanically engages the plug to help retain the plug within the socket well. In examples, the plug is configured to actuate a switch in the control circuit to cause the control circuit to provide the electrical power to the actuator when the plug mechanically couples with the socket. In some examples, the socket includes a sliding pin configured to physically translate and close the switch, and the plug is configured to contact and cause translation of the sliding pin to close the switch.

In examples, the plug defines a plug body and the socket defines a socket body, and some portion of the plug body (e.g., plug seat 139 (FIG. 2)) is configured to contact some portion of the socket body when the plug mechanically couples with the socket. The plug body may include a surface defining a plug seat and the socket body may define a surface defining a socket seat, and the plug seat may be configured to contact the socket seat when the plug mechanically couples with the socket. The plug may be configured to translate in a direction substantially along a socket axis defined by the socket to mechanically couple with the socket. In examples, the socket body defines a socket well configured to receive a portion of the plug body when the plug mechanically couples with the socket. In some examples, the socket defines a socket opening configured to receive the plug when the plug mechanically couples with the socket. The socket may be configured such that the socket axis extends through the socket opening and the socket seat.

The actuator of the connector may be configured to translate the clamp head in a clamping direction to cause the clamp head to mechanically engage the plug. In examples, the actuator is also configured to translate the clamp head in an unclamping direction substantially opposite the clamping direction to cause the clamp head to disengage from the plug. For example, when the plug is mechanically coupled with the socket and the clamp head is mechanically engaged with plug, the actuator may be configured to translate the clamp head in the unclamping direction to disengage the clamp head and the plug such that the plug may be uncoupled from the socket.

The control circuit may be configured to selectively cause the actuator to translate the clamp head in either the clamping direction or the unclamping direction. In examples, the connector includes an input device (e.g., a button, switch, touchscreen, or the like) configured to cause the actuator to translate the clamp head in the unclamping direction. The input device may be configured to receive a user input from a patient or other user. The control circuit may be configured to cause the actuator to translate the clamp head in the unclamping direction in response to the user input such that, for example, the patient or another user may translate the plug away from the socket to uncouple the plug and the socket.

The clamp head may have any configuration sufficient to mechanically engage the plug when the actuator translates the clamp head. In examples, the clamp head is configured to mechanically engage the plug body. The clamp head may be configured to substantially surround some portion of a perimeter of the plug body when the clamp head mechanically engages the plug body. For example, the plug body may define a substantially circular perimeter, and the clamp head may define a substantially arc shaped and/or semicircular shaped clamp face configured to mechanically engage a portion of the circular perimeter. The clamp head may be configured to establish a frictional contact with the plug body when the clamp head mechanically engages the plug body. In examples, the clamp head exerts a force against the plug body when the clamp head mechanically engages the plug body, and the exerted force and the frictional contact produce a frictional force on the plug body tending to resist movement of the plug relative to the socket.

In examples, the clamp head is a first clamp head and the socket includes a second clamp head. The actuator may be configured to translate both the first clamp head and the second clamp head to cause the first clamp head and second clamp head to mechanically engage the plug when the plug mechanically couples with the socket. In some examples, the first clamp head and the second clamp head are configured to substantially surround the plug (e.g., 85% to 100% of an outer perimeter of the plug body, such as 90% to 100% or 95% to 100% of the outer perimeter) when the first clamp head and the second clamp head mechanically engage the plug. The first clamp head and/or second clamp head may be configured to translate in a direction toward the plug body when the plug mechanically couples with the socket.

In some examples, the plug body is be configured such that, when the plug mechanically couples with the socket, a portion of the second conduit (e.g., an end of a machine line) inserts into the plug outlet. The connector may be configured such that the first clamp and/or second clamp (if present) mechanically engage the plug to retain the portion of the second conduit within the plug outlet and prevent inadvertent disconnection of the plug and the second conduit. In examples, the socket is configured to substantially align the portion of the second conduit and the plug outlet, such that the portion of the second conduit inserts into the plug outlet when the plug mechanically couples with the socket.

In some examples, the connector is configured to assist in the proper connection of containers and the medical machine. This may help increase the success of an at-home therapies, e.g., dialysis, that require a patient or other user to make connections between a material source and a medical machine by at least helping to prevent the patient (or other user) from connecting a material source to the wrong fluid line of the medical machine. Such improper connections may interfere with the success of the at-home therapy.

For example, the connector may include one or more visible indicia that helps the user align the connector for a particular container with the correct fluid line of the medical machine. As an example, a plug attached to a particular container may have a color and/or include a symbol (e.g., a graphical symbol) corresponding to a color and/or symbol of a specific socket of a medical machine. The specific socket of a connector may be configured to provide the contents of the particular container to the medical machine, such that the medical machine generates a medication using the contents of the particular medical solution container. Substantially matching the corresponding color and/or symbols of the plug and the socket may assist the patient or other user in the proper placement of the plug in the correct socket. In addition to, or instead of, the visible indicium, in some examples, a particular plug may be configured to mate with a respective socket and to not mate with other sockets of the medical machine to help a user better understand which socket a particular plug should be introduced into in order to properly connect a container connected to the plug with the medical machine.

FIG. 1 is a block diagram illustrating an example medical system 100 using an example connector 102. Medical system 100 includes a medical machine 104 configured to provide therapy (e.g., dialysis) to a patient using one or more materials stored by one or more external containers 106, 107. For example, medical system 100 may be configured to produce a medication for a patient therapy using one or more concentrates. For example, medical machine 104 may be configured to produce dialysate for the patient using concentrates contained in one or more containers such as container 106 and container 107. Medical system 100 may be configured to generate the medical solution by at least mixing a concentrate within container 106 with a fluid such as water. In examples, medical system 100 is configured to receive the fluid via fluid line 114 and deliver the medical solution produced (e.g., dialysate) via an infusion line 112. For example, infusion line 112 may provide dialysate to a cycler configured to provide therapy to a patient using the dialysate, or to a container configured to retain the dialysate for subsequent use.

Medical system 100 may include a conditioning system 116 configured to provide fluid received via infusion line 112 to a generation flow path 118 defined by medical machine 104. Conditioning system 116 may include, for example, a pump configured to provide a motive force to the fluid received via infusion line 112 to drive the fluid through generation flow path 118. In some examples, conditioning system 116 may include one or more filters and/or sorbent cartridges configured to remove impurities (e.g., particulate matter and/or ions) from the fluid prior to the fluid entering generation flow path 118. In addition, in some examples, conditioning system 116 may include one or more sensors, such as a conductivity sensor and/or a pressure sensor, configured to monitor a physical state or condition of the fluid prior to the fluid entering generation flow path 118. In examples, conditioning system 116 includes a degasser configured to degas the fluid prior to entering generation flow path 118. The degasser may include, for example, a vacuum pump configured to create a vacuum to remove air and other gases from the fluid prior to entering generation flow path 118.

Medical system 100 may be configured to generate a medical solution using the one or more concentrates held in one or more containers such as container 106 and container 107. In examples, medical system 100 may be configured to provide a fluid (e.g., purified water) to container system 119 such that container system 119 may generate the medical solution. For example, medical system 100 may be configured to receive a fluid via fluid line 114 and provide the fluid (e.g., from conditioning system 116) to container system 119 using machine fluid line 123. In some examples, container system 119 may be configured to utilize a single fluid path for both an injection of fluid (e.g., purified water) into container system and extraction of a medical solution. For example, container system 119 may be configured to receive the fluid via second conduit 110 and first conduit 108 in a first flow direction to generate a medical solution, and then supply the medical solution via second conduit 110 and first conduit 108 in a second flow direction opposite the first flow direction.

In examples, medical system 100 includes one or more concentrate pumps such as concentrate pump 120 configured to inject a concentrate from container 106 into generation flow path 118 via second conduit 110. In some examples, medical system 100 may include one or more additional filters (not shown) configured to filter the concentrate provided from container 106 prior to the concentrate entering generation flow path 118. The concentrate may include one or more solutes. In examples, the solute includes an osmotic agent such as glucose, dextrin, and/or icodextrin. In examples, the solute includes an ion such as sodium chloride, sodium lactate, magnesium chloride, calcium chloride, potassium chloride, and/or sodium bicarbonate.

Connector 102 is configured to fluidly couple first conduit 108 and second conduit 110, to enable medical system 100 to provide a concentrate held within container 106 to generation flow path 118. Connector 102 includes a plug 122 mechanically engaged with first conduit 108 and a socket 124 mechanically engaged with second conduit 110. Plug 122 is configured to mechanically couple with socket 124 such that a confined fluid path is established from an interior of container 106, through first conduit 108, and to second conduit 110. As described in further detail below, in some examples, connector 102 defines the confined fluid path through a plug channel (not shown in FIG. 1) defined by a body of plug 122. The plug channel may extend from a plug inlet (not shown in FIG. 1) defined by plug 122 to a plug outlet (not shown in FIG. 1) defined by plug 122. The plug inlet may be configured to mechanically engage first conduit 108 such that first conduit 108 is fluidically coupled with the plug outlet.

Plug 122 may be configured to mechanically couple with socket 124 such that the plug outlet is fluidically coupled to second conduit 110 when second conduit 110 is mechanically engaged by socket 124. In examples, socket 124 defines a recessed socket well, and plug 122 is configured to insert into the socket well to mechanically couple with socket 124. For example, plug 122 can have a hollow cylindrical body configured to be received in a cylindrical socket well. In some examples, socket 124 is mechanically supported by a housing 105 of medical machine 104. Hence, connector 102 may be configured to define a confined fluid path from an interior of container 106 to generation flow path 118, such that medical system 100 may generate a medical solution using a concentrate held in container 106 and a fluid introduced via fluid line 114.

Connector 102 is configured to substantially minimize or avoid inadvertent disconnections of plug 122 and socket 124, such that the production of medical solution by medical system 100 is not unintentionally interrupted. When first conduit 108 is connected to plug 122, connector 102 is configured to minimize or even prevent inadvertent disruption of the fluid communication between first conduit 108 and second conduit 110. Connector 102 includes a clamp head 126 configured to mechanically engage plug 122 when plug 122 mechanically couples with socket 124. Clamp head 126 may be configured to limit movement of plug 122 relative to socket 124 in one or more directions tending to disrupt and/or degrade the mechanical mating of plug 122 and socket 124. In examples, clamp head 126 is configured to translate in a direction toward plug 122 when plug 122 mechanically mates with socket 124.

Clamp head 126 may be configured to contact plug 122 and exert a force on plug 122 tending to help sustain the mechanical coupling of plug 122 and socket 124. In examples, plug 122 is configured to mechanically couple with socket 124 when plug 122 translates (e.g., is translated by a patient or a clinician) in a first direction toward socket 124, and clamp head 126 is configured to mechanically engage plug 122 to resist translation of plug 122 in a second direction opposite the first direction. In some examples, socket 124 defines a socket well and plug 122 is configured to insert into the socket well to mechanically couple with socket 124, and clamp head 126 is configured to exert a force on plug 122 in a direction tending to retain plug 122 within the socket well, and, therefore, maintain a fluid connection between first conduit 108 and second conduit 110 (and, therefore, between container 106 and second conduit 110).

In examples, medical machine 104 may be configured to receive the particular contents of container 106 within second conduit 110 and, therefore, a particular socket such as socket 124, as opposed to another socket which may be present in medical machine 104, such as socket 121. In some examples, connector 102 is configured to help facilitate the proper connection between container 106 and a specific socket 124. For example, connector 102 can include one or more visible indicia to assist in the proper connection of specific plugs with specific sockets, such as the connection of plug 122 and socket 124. For example, plug 122 may be a component of container system 119 including container 106, first conduit 108, and plug 122. First conduit 108 may be a flexible tube (e.g., disposable or reusable) fluidly coupled to an interior of container 106. Medical machine 104 may be configured to receive the particular contents of container 106 via socket 124, in order to produce a particular medical solution for the treatment of a patient. Plug 122 may include a color and/or include a symbol corresponding to a color and/or symbol, respectively, of socket 124 of medical machine 104 to assist the patient or other user in the proper placement of a specific plug such as plug 122 in a specific socket such as socket 124. In examples, plug 122 is a disposable plug configured to be disposed of when one or more components of container system 119 are replaced. In examples, plug 122 is substantially affixed and/or attached to first conduit 108 and configured to be delivered to medical system 100 as part of container system 119.

Connector 102 is configured such that the mechanical coupling of plug 122 and socket 124 causes clamp head 126 to mechanically engage plug 122. Connector 102 may include an actuator (not shown in FIG. 1) configured to translate clamp head 126 when plug 122 mechanically couples with socket 124, such that clamp head 126 mechanically engages plug 122. The actuator may be configured to receive electrical power from a control circuit and use the electrical power to cause the translation of clamp head 126.

Plug 122 may be configured to cause the control circuit to provide the electrical power to the actuator when plug 122 mechanically mates with the socket. In examples, the control circuit includes a switch configured to cause the control circuit to provide the electrical power to translate clamp head 126, and plug 122 is configured to actuate the switch when plug 122 mechanically couples with socket 124.

Container system 119 may further includes a fluid connector 129 configured to fluidly couple container 106 and machine fluid line 123. In examples, fluid connector 129 is configured to mechanically mate with a fluid connector 131 of machine fluid line 123 to provide the fluid coupling. In some examples, as discussed above, container system 119 may be configured to utilize a single fluid path for both an injection of fluid and extraction of medical solution. Hence, container system 119 may be a separable system configured to attach to and/or detach from medical machine 104. Fluid connector 129 and/or socket 122 may be configured such that a patient or care-giver may connect container system 119 to medical machine 104 in preparation for use of a medical solution provided by container system 119.

Medical system 100 may further include a mixing system 117 configured to provide the medical solution to infusion line 112. In examples, mixing system 117 includes a mixing chamber configured to further mix the concentrate from container 106 and the fluid from conditioning system 116. Mixing system 117 may include one or more sensors configured to evaluate one or more physical characteristics of the medical solution, such as one or more of conductivity sensors, pH sensors, pressure sensors, flow sensors, or the like. In some examples, mixing system 117 includes one or more sterilization units, such as one or more ultrafilters, microbial filters, UV light sources, or other sterilization units configured to substantially sterilize dialysate prior to infusion into a patient.

Hence, connector 102 may be configured to fluidly couple first conduit 108 and second conduit 110, such that medical system 100 may produce a medication (e.g., dialysate) using one or more medical materials stored by container 106 and delivered via first conduit 108. Connector 102 may provide the fluidic coupling using plug 122 configured to mechanically couple with socket 124. Connector 102 includes clamp head 126 configured to mechanically engage plug 122 when plug 122 mechanically mates with socket 124. Clamp head 126 may be configured to exert a force on plug 122 to help sustain the mechanical mating in order to, for example, substantially minimize or avoid inadvertent disconnections of plug 122 and socket 124 as medical system 100 provides a medical solution (e.g., dialysate).

Figure 2:
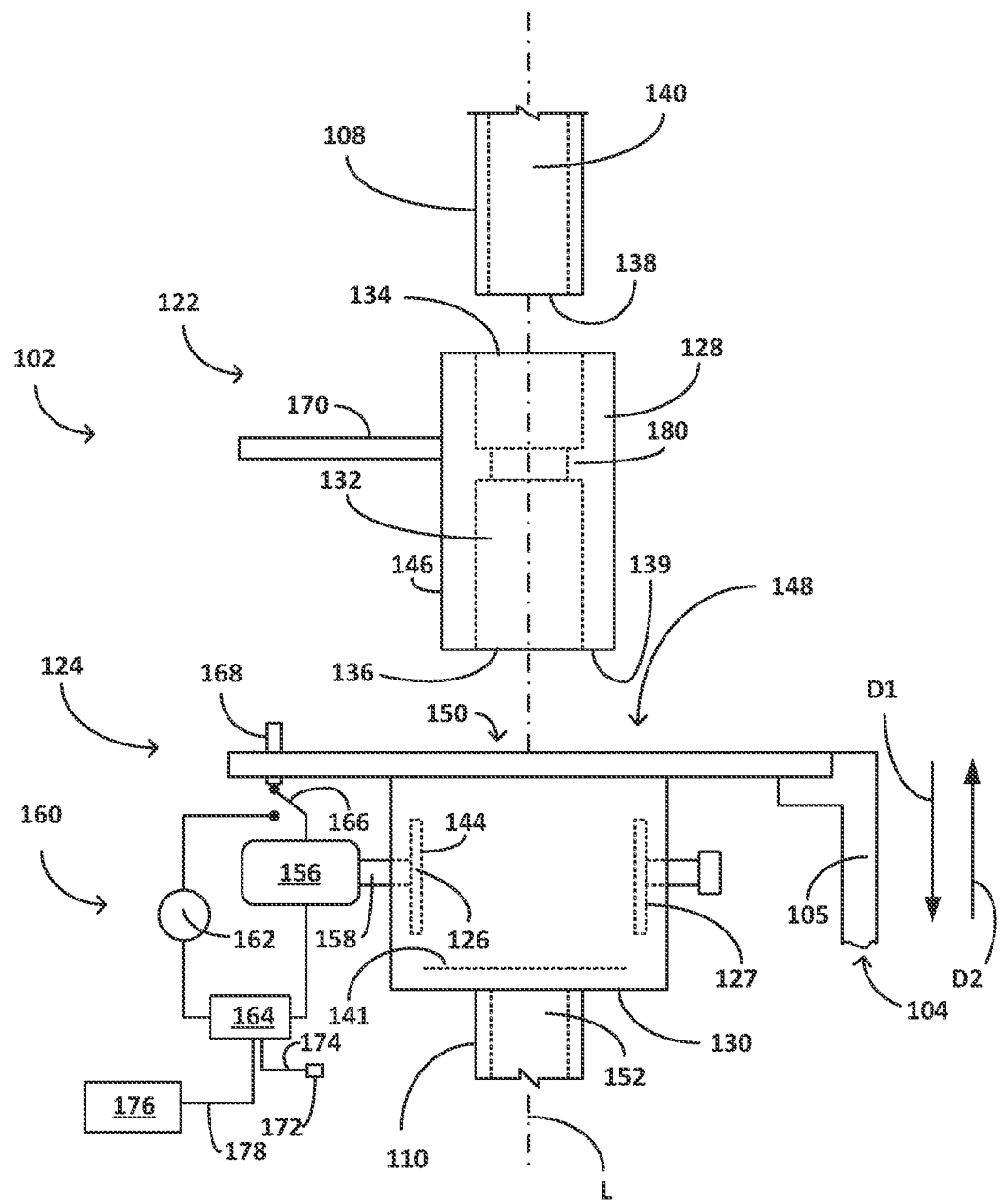
FIG. 2 is a conceptual diagram of an example connector including a plug and a socket.

FIG. 2 illustrates an example connector 102 including plug 122 including plug body 128. Connector 102 further includes socket 124 including socket body 130. Plug 122 is configured to mechanically engage first conduit 108 (e.g., tubing from a container 106) and socket 124 is configured to mechanically engage second conduit 110 (e.g., a machine line). Plug 122 is configured to mechanically couple with socket 124 such that the first conduit 108 and the second conduit 110 are fluidly coupled. Connector 102 is configured to translate a clamp head 126 to cause clamp head 126 to mechanically engage plug 122 to help sustain the mechanical coupling between plug 122 and socket 124 as connector 102 provides fluid coupling between first conduit 108 and second conduit 110. Plug 122 is configured to cause connector 102 to translate clamp head 126 when plug 122 mechanically couples with socket 124, such that clamp head 126 mechanically engages plug 122 to minimize movements of plug 122 which might tend to cause an uncoupling of plug 122 and socket 124. In examples, plug 122 is configured to mechanically couple with socket 124 when plug 122 is translated toward socket 124 in a first direction D1 and configured to uncouple with socket 124 when plug 122 is translated away from socket 124 in a second direction D2 substantially opposite first direction D1. Clamp head 126 may be configured to mechanically engage plug 122 to resist translation of plug 122 in the second direction D2 to help sustain the mechanical coupling between plug 122 and socket 124.

Figure 3:
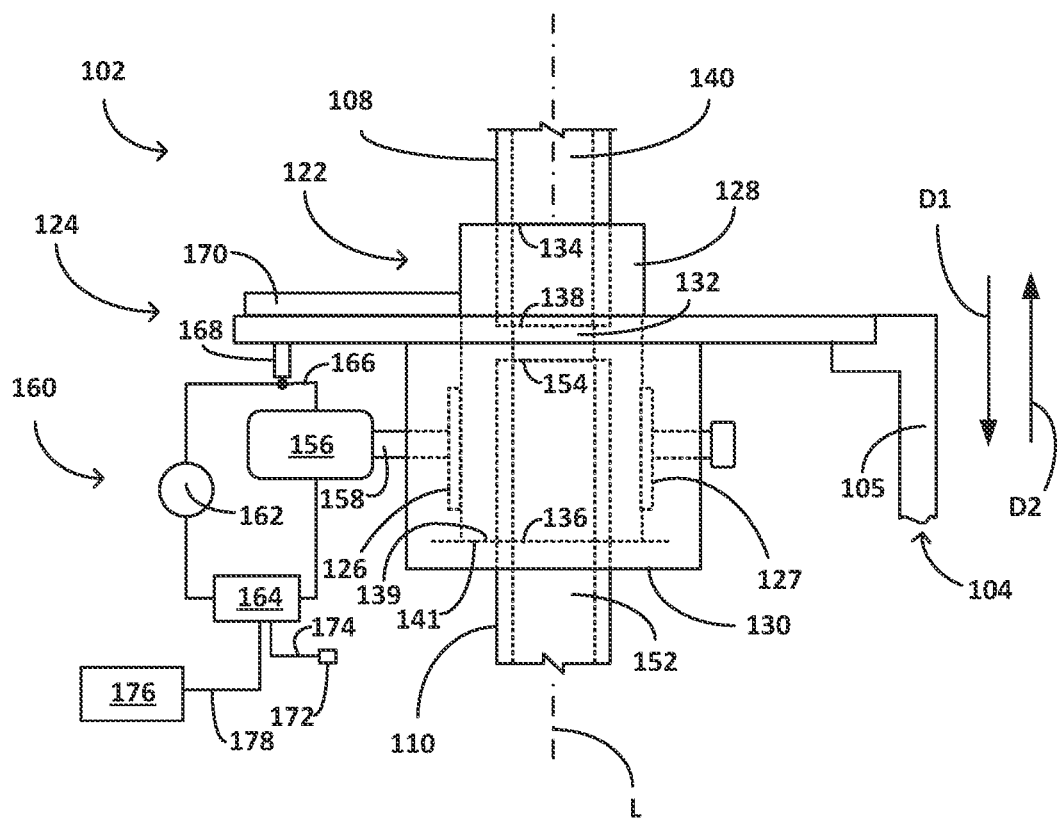
FIG. 3 is a conceptual diagram of the connector of FIG. 2 with the plug mechanically mated with the socket.
Figure 4:
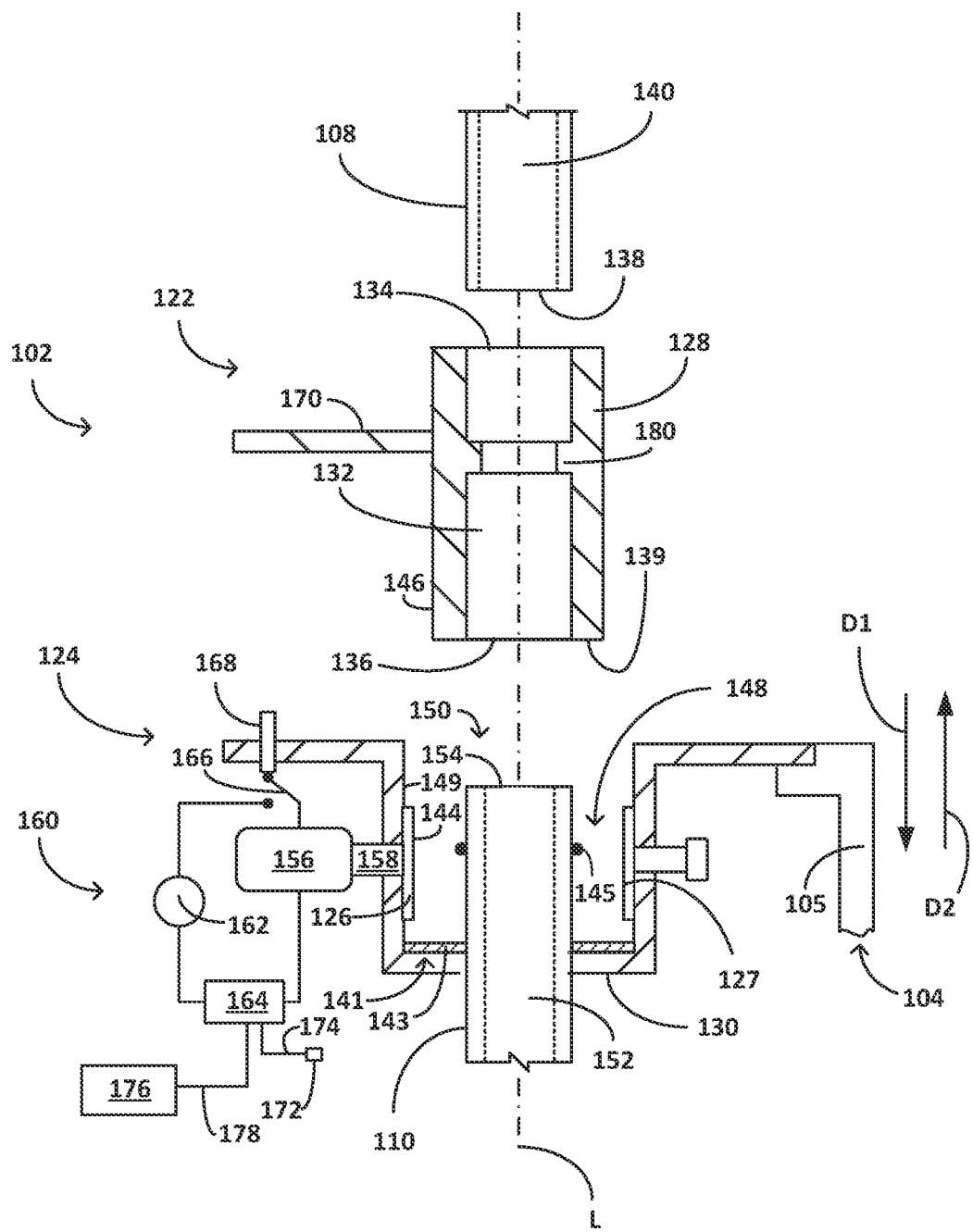
FIG. 4 is a conceptual diagram illustrating a cross-section of the connector of FIG. 2, the cross-section being taken through a central longitudinal axis of the connector.
Figure 5:
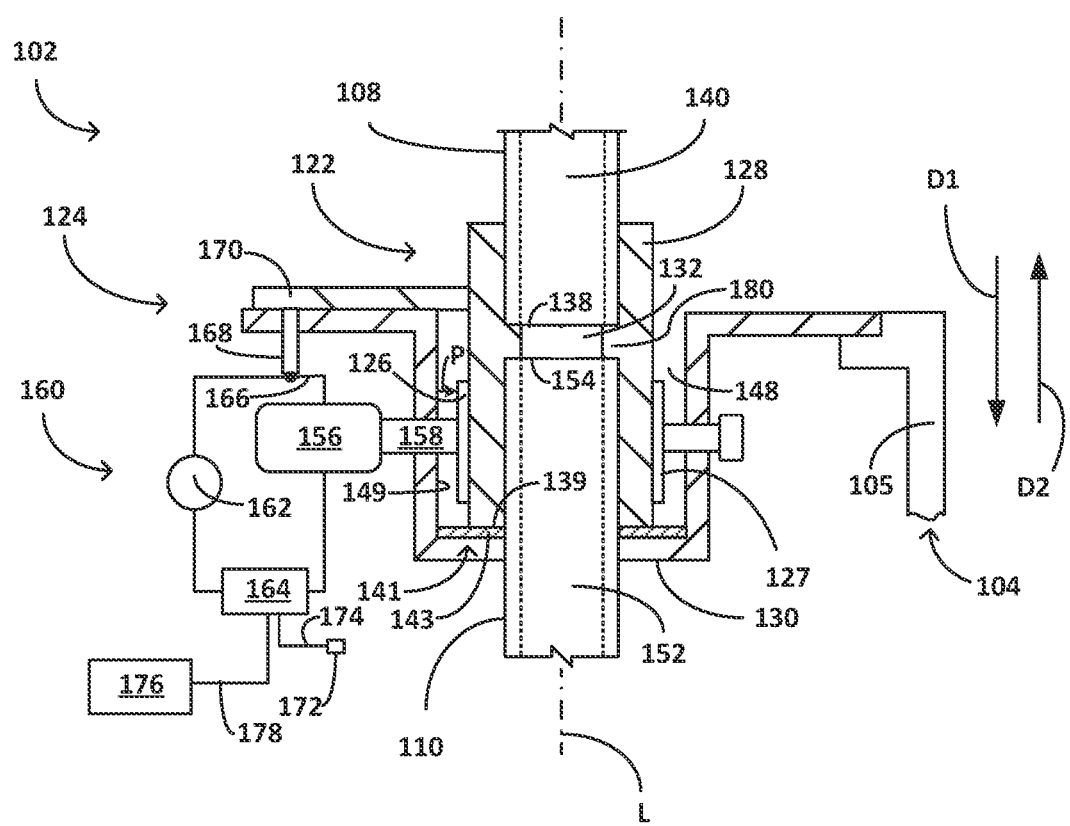
FIG. 5 is a conceptual diagram illustrating a cross-section of the connector of FIG. 2 with the plug mechanically mated with the socket, the cross-section being taken through the central longitudinal axis of the connector.
Figure 6:
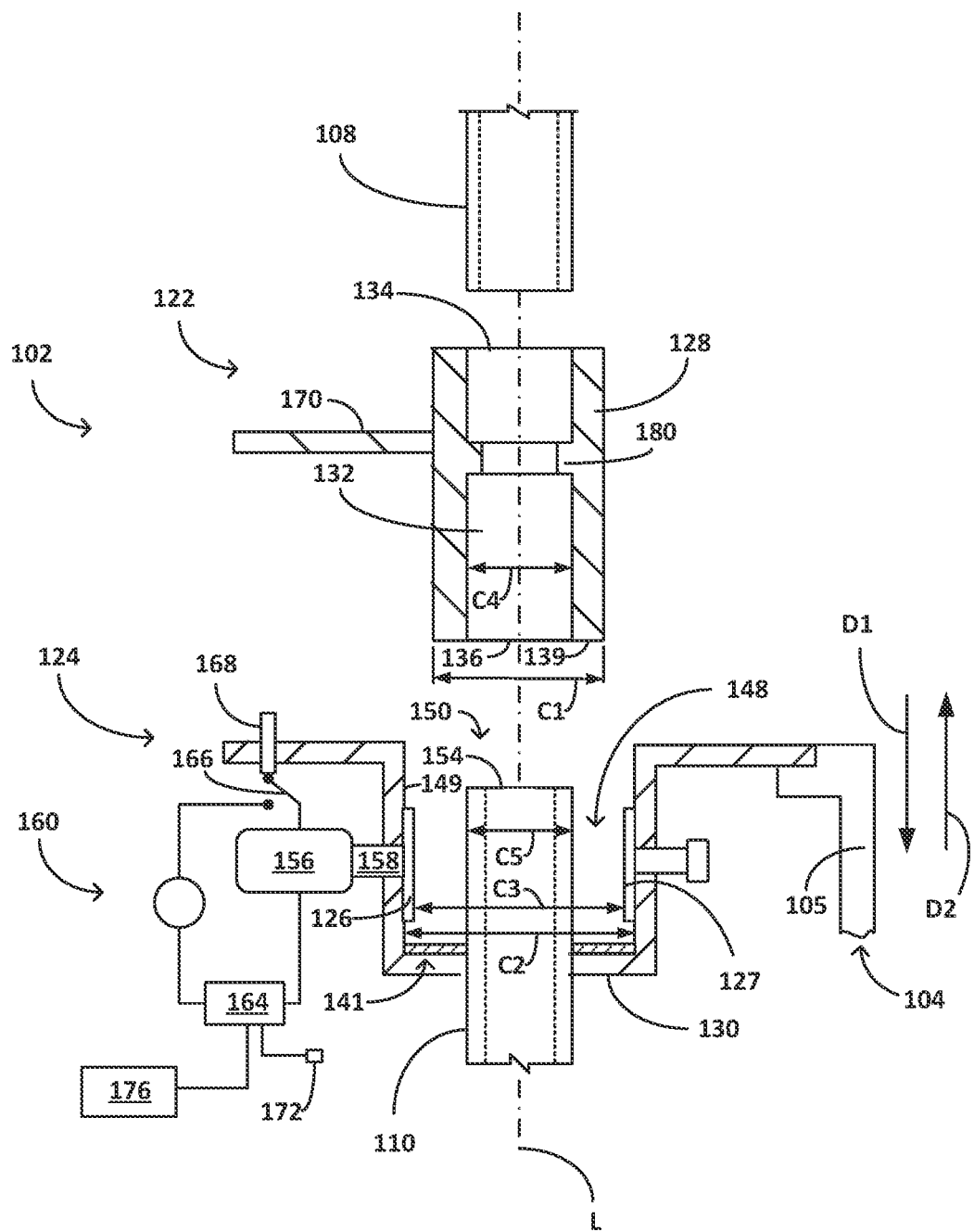
FIG. 6 is a conceptual diagram illustrating dimensions of the cross-section of the connector of FIG. 2.

FIG. 3 illustrates connector 102 with plug 122 mechanically coupled with socket 124 and providing fluid coupling between first conduit 108 and second conduit 110. FIG. 4 illustrates a cross-section of connector 102 with the cutting plane parallel to the page and through a central longitudinal axis of connector 102 (e.g., extending through a central longitudinal axis of plug 122 and socket 124), referred to herein as a socket axis L. FIG. 5 illustrates a cross-section of connector 102 with plug 122 mechanically coupled with socket 124, with the cutting plane parallel to the page and through the central longitudinal axis of connector 102. FIG. 6 illustrates cross-sectional dimensions of connector 102, with the cutting plane parallel to the page and through the central longitudinal axis of connector 102.

Plug 122 defines a channel 132 ("plug channel 132") extending through plug body 128 and opening to a plug inlet 134 and a plug outlet 136. Plug channel 132 is illustrated with dashed lines in FIGS. 2 and 3. Plug inlet 134 and plug outlet 136 are openings defined by plug body 128. Plug channel 132 is configured to establish fluid communication between plug inlet 134 and plug outlet 136. Plug 122 is configured to mechanically engage first conduit 108 to connect first conduit 108 and plug outlet 136, such that a fluid may flow from a first fluid channel 140 defined by first conduit 108 to plug outlet 136 through plug channel 132.

Plug 122 may be configured to mechanically engage first conduit 108 in any manner sufficient to fluidly couple first conduit 108 and plug outlet 136. In examples, plug 122 is configured to mechanically engage first conduit 108 such that plug 122 establishes a substantially confined (e.g., confined but for manufacturing tolerances) flow path from first fluid channel 140 to plug outlet 136. In examples, plug inlet 134 is configured to receive first conduit 108 (e.g., a flexible or rigid tube). For example, plug inlet 134 can be configured to allow an end 138 of first conduit 108 ("first conduit end 138") to insert into plug channel 132 through plug inlet 134 in order to fluidly couple first conduit 108 and plug outlet 136. For example, FIGS. 3 and 5 illustrate first conduit 108 inserted through plug inlet 134, such that first conduit end 138 is positioned within plug channel 132 of plug 122.

Plug 122 is configured to mechanically couple with socket 124 to, for example, fluidly couple first conduit 108 and second conduit 110. Plug 122 may be configured to translate in a direction substantially along a socket axis L (e.g., a central longitudinal axis) defined by socket 124 to mechanically couple with the socket 124. In examples, a body 128 of plug 122 ("plug body 128") is configured to contact some portion of a body 130 of socket 124 ("socket body 130") when plug 122 mechanically couples with socket 124. In examples, plug body 128 defines a plug seat 139 and socket body 130 at least partially defines a socket seat 141, and plug seat 139 is configured to contact socket seat 141 when plug 122 mechanically couples with socket 124.

In some examples, socket seat 141 includes a compressible material 143 (FIGS. 4, 5) such as an O-ring or another fluid seal. Compressible material 143 may be configured to compress when contacted by plug seat 139, such that plug seat 139 and socket seat 141 form a substantially fluidically sealed contact (e.g., completely fluid sealed or nearly completely fluid sealed to the extent permitted by manufacturing tolerances). In some examples, instead of or in addition to compressible material 143, plug body 128 (e.g., an inner surface defining plug channel 132) is configured to contact a sealing system 145 (FIG. 4) to form a substantially fluidically sealed contact with second fluid conduit 110 when plug body 128 mechanically engages second fluid conduit 110. In examples, sealing system 145 is an O-ring substantially surrounding a portion of second fluid conduit 110 within socket well 148.

Connector 102 is configured to translate clamp head 126 to cause clamp head 126 to mechanically engage plug 122 when plug 122 mechanically couples with socket 124. In examples, connector 102 is configured to translate clamp head 126 relative to a portion of socket 124, such as socket body 130. Clamp head 126 may be configured such that the mechanical engagement with plug 122 limits movements of plug 122 relative to socket 124 in directions which might trend to cause plug 122 to uncouple with socket 124, such as movements in directions substantially perpendicular to first direction D1, or movements in the direction D2. In examples, clamp head 126 is configured to establish a frictional contact with plug body 128 when clamp head 126 mechanically engages plug body 128. In examples, clamp head 126 is configured to exert a force against plug body 128 when clamp head 126 mechanically engages plug body 128. Clamp head 126 may be configured such that force exerted by clamp head 126 and the frictional contact between clamp head 126 and plug body 128 produces a frictional force on plug body 128 tending to resist movement of plug 122 relative to socket 124. For example, when plug 122 experiences a force in the direction D2 (indicative of a force on plug 122 tending to cause plug 122 to uncouple from socket 124), the frictional force may exert a force on the plug in the direction D2 to limit movement of plug 122.

In some examples, one of clamp head 126 or plug body 128 defines a protrusion and the other of clamp head 126 or plug body 128 defines a recess, and the protrusion is configured to insert into the recess when clamp head 126 mechanically engages plug 122. For example, plug body 128 may define a plug recess configured to receive clamp head 126. The recess may be configured such that, when the protrusion is inserted in the plug recess (e.g., when clamp head 126 mechanically engages plug 122), movement of plug 122 relative to socket 124 causes the protrusion and the recess to generate an action-reaction force pair limiting the relative movement. For example, when plug 122 defines the recess and plug 122 experiences a force in the direction D2, the recess may exert a force on the protrusion of clamp head 126 in the direction D2, causing the protrusion to exert a reaction force in the direction D1 on the recess to limit movement of plug 122. When plug 122 defines the protrusion and plug 122 experiences the force in the direction D2, the protrusion may exert a force on the recess of socket 124 in the direction D2, causing the recess to exert a reaction force in the direction D2 on the protrusion to limit movement of plug 122.

In some examples, one or more surfaces of clamp head 126 may be configured to substantially conform to one or more surfaces of plug 122 when plug 122 mechanically couples with plug 122. In examples, clamp head 126 includes a clamp face 144 configured to contact plug 122 (e.g., plug body 128) when clamp head 126 mechanically engages plug 122. Clamp face 144 may be configured to define a complementary shape to a shape of a plug surface 146 of plug body 128, such that clamp face 144 and plug surface 146 limit movement of plug 122 relative to socket 124 at least in a direction substantially perpendicular (e.g., perpendicular or within 5 degrees or less of exactly perpendicular) to the first direction D1. In examples, clamp face 144 is configured to surround some portion of a perimeter of plug body 128 when clamp head 126 mechanically engages plug body 128. In some examples, plug body 128 defines a substantially circular perimeter, and clamp face 144 defines a substantially circular arc such as a semi-circle configured to mechanically engage a portion of the substantially circular perimeter.

In examples, one of plug 122 or socket 124 defines a protuberance and the other of plug 122 or socket 124 defines a cavity, and the cavity is configured to receive the protuberance when socket 124 mechanically mates with plug 122. In some example, plug 122 defines the protuberance and socket 124 defines the cavity. As illustrated in FIGS. 2, 3, 4 and 5, socket 124 may be configured such that socket body 130 defines a socket well 148 recessed into socket body 130. Socket well 148 may be configured such that plug 122 (e.g., a portion of plug body 128) inserts into socket well 148 to mechanically couple with socket 124. Plug 122 may be configured to translate in a direction substantially along socket axis L (e.g., a central axis) to mechanically couple with socket 124. In examples, socket 124 defines a socket opening 150 opening to socket well 148 and configured to receive plug 122 when plug 122 mechanically couples with socket 124. Socket 124 may be configured such that socket axis L extends through socket opening 150.

Socket 124 is configured to mechanically engage second conduit 110. Second conduit 110 may be, for example, a machine line of medical machine 104. In examples, socket 124 is configured to mechanically engage second conduit 110 such that, when plug 122 mechanically mates with socket 124, plug channel 132 fluidly couples with second conduit 110. Socket 124 may be configured such that the mechanical mating of plug 122 and socket 124 establishes a substantially confined flow path from plug channel 132 to a second fluid channel 152 defined by second conduit 110. Hence, connector 102 may be configured to form a physical connection between first conduit 108 (e.g., tubing for a container 106 (FIG. 1)) and second conduit 110 (e.g., a machine line for medical machine 104 (FIG. 1)) when plug 122 mechanically mates with socket 124. In examples, housing 105 of medical machine 104 mechanically supports socket 124 and/or second conduit 110. In examples, socket 124 may be affixed to or an integral part of medical machine 104 and/or housing 105. Second conduit 110 may be affixed to or an integral part of socket 124, medical machine 104, and/or housing 105.

Socket 124 may be configured to mechanically engage second conduit 110 in any manner sufficient to fluidly couple plug channel 132 with second conduit 110 when plug 122 mechanically mates with socket 124. In examples, socket 124 is configured to mechanically engage second conduit 110 such that plug 122 establishes a substantially confined flow path from plug channel 132 to second fluid channel 152 of second conduit 110. Socket 124 may be configured to mechanically engage second conduit 110 such that plug 122 establishes a substantially confined flow path from first fluid channel 140 of first conduit 108 to second fluid channel 152 of second conduit 110. In examples, socket 124 is configured to mechanically engage second conduit 110 such that an end 154 of second conduit 110 ("second conduit end 154") inserts into plug channel 132 through plug outlet 136 when plug 122 mechanically mates with socket 124. For example, FIG. 3 illustrates second conduit 110 inserted through plug outlet 136, such that second conduit end 154 is positioned within plug channel 132 of plug 122. In examples, socket axis L extends through socket opening 150 and second conduit 110 when socket 124 mechanically engages second conduit 110.

Connector 102 can include any suitable number of clamp heads (e.g., one, two, three, four, or more), each configured to engage with plug 122 to help hold plug 122 in socket 124. For example, in some examples, connector 102 includes a second clamp head 127 in addition to clamp head 126, where second clamp head 127 is configured to mechanically engage plug 122 when plug 122 mechanically couples with socket 124. Connector 102 is configured to translate clamp head 127 to cause clamp head 127 to mechanically engage plug 122. Clamp head 127 may be configured similarly to clamp head 126. Connector 102 may be configured to translate both clamp head 126 and clamp head 127 head to cause clamp head 126 and clamp head 127 to mechanically engage plug 122 when plug 122 mechanically couples with socket 124.

In examples, clamp head 126 is configured to exert a first force on plug 122 when clamp head 126 mechanically engages plug 122 and clamp head 127 is configured to exert a second force on plug 122 when clamp head 127 mechanically engages plug 122. In some examples, clamp head 126 and clamp head 127 may be configured such that the first force opposes the second force. In some examples, clamp head 126 and clamp head 127 are configured to substantially surround plug 122 (e.g., substantially surround an outer perimeter defined by plug body 128) when clamp head 126 and the clamp head 127 mechanically engage plug 122. In some examples, plug body 128 defines a substantially circular outer perimeter, and clamp head 126 and clamp head 127 each define a substantially semicircular arc, such that clamp head 126 and clamp head 127 together substantially surround (e.g., about 345 degrees to 360 degrees, such as about 355 degrees to 360 degrees, or 360 degrees) the circular outer perimeter when clamp head 126 and clamp head 127 mechanically engage plug 122. Clamp head 126 and/or clamp head 127 may engage and/or substantially surround plug body 128 around any arc angle and/or portion of an outer perimeter defined by plug body 128. Connector 102 may include any number of clamp heads configured to mechanically engage plug 122 when plug 122 mechanically couples with socket 124.

In examples, clamp heads 126, 127 are configured to translate in a direction toward plug body 128 when plug 122 mechanically couples with socket 124. Clamp heads 126, 127 may be configured to translate in a direction from a wall 149 of socket well 148 ("socket wall 149") (FIG. 4) toward plug body 128 when plug body 128 is inserted in socket well 148. Clamp heads 126, 127 may be positioned adjacent to socket wall 149 and within socket well 148 and configured to displace from socket wall 149 when the respective clamp head 126, 127 translates to mechanically engage plug 122. For example, FIG. 4 illustrates clamp head 126 substantially adjacent (e.g., in contact with) socket wall 149. Clamp head 126 may be configured to displace from socket wall 149 over a displacement P, as illustrated in FIG. 5, to mechanically engage plug body 128 when plug 122 mechanically couples with socket 124. In examples, clamp heads 126, 127 are configured to translate from the position adjacent socket wall 149 toward socket axis L to mechanically engage plug 122. In some examples, clamp heads 126, 127 are configured to displace from socket wall 149 in a direction substantially perpendicular to the direction D1 and/or socket axis L. In some examples, socket wall 149 separates socket seat 141 from socket opening 150.

Connector 102 includes an actuator 156 configured to translate clamp head 126, 127 to cause clamp head 126 and, if present, other clamp head 127 to mechanically engage plug 122. While both clamp heads 126, 127 are referred to in the description of actuator 156 and control circuit 160, the description may apply to a single clamp head if only one is present or to more than two clamp heads if more than two are present.

Actuator 156 is configured to translate clamp heads 126, 127 when actuator 156 receives electrical power. In examples, actuator 156 includes a motor configured to receive electrical power and convert some portion of the electrical power into a mechanical motion causing translation of clamp heads 126, 127 toward plug body 128. In some examples, actuator 156 includes an electromagnet configured to receive electrical power and cause translation of clamp heads 126, 127 toward plug body 128. Actuator 156 may be configured to convert the portion of the electrical power into a linear motion. In examples, actuator 156 includes an output shaft 158 coupled to clamp heads 126, 127, and actuator 156 is configured to linearly translate output shaft 158 to cause clamp heads 126, 127 to translate (e.g., over the displacement P) to mechanically engage plug 122. Actuator 156 may be configured to cause clamp heads 126, 127 to translate such that clamp heads 126, 127 moves relative to socket body 130 (e.g., relative to socket wall 149). Connector 102 may be configured such that some portion of socket body 130 (e. g., socket wall 149) is positioned between actuator 156 and clamp heads 126, 127. Output shaft 158 may be configured to pass through a passage of socket body 130 to cause translation of clamp heads 126, 127. In some examples, connector 102 is configured such that clamp heads 126, 127 are positioned substantially within socket well 148 and actuator 156 is positioned outside socket well 148.

Actuator 156 may have any configuration sufficient to cause the translation of clamp heads 126, 127. In examples, actuator 156 includes an electromagnetic motor. In some examples, actuator 156 may include a linear motor configured to generate a linear force when actuator 156 receives electrical power. In other examples, actuator 156 may include a rotary motor configured to produce a rotary motion when actuator 156 receives electrical power, and actuator 156 may be configured to convert (e.g., using one or more gears and/or pinions) the rotary motion into a linear force. In some examples, actuator 156 may include an electromagnet configured to generate a linear force when actuator 156 receives electrical power. Actuator 156 may be configured to exert some portion of the linear force on output shaft 158 to cause the translation of clamp heads 126, 127. In other examples, actuator 156 may be configured to generate a linear force using a working fluid, such as air, oil, or some other fluid. Actuator 156 may be configured to cause the working fluid to generate a linear force on output shaft 158 when actuator 156 receives electrical power.

Actuator 156 may be configured to translate clamp heads 126, 127 in a clamping direction to cause clamp heads 126, 127 to mechanically engage plug 122. The clamping direction may be direction extending from clamp heads 126, 127 and toward plug 122. In examples, actuator 156 is also configured to translate clamp heads 126, 127 in an unclamping direction substantially opposite the clamping direction. Clamp heads 126, 127 may be configured to disengage from plug 122 when actuator 156 translates clamp heads 126, 127 in the unclamping direction. For example, when plug 122 is mechanically coupled with socket 124 and clamp heads 126, 127 is mechanically engaged with plug 122, actuator 156 may be configured to translate clamp heads 126, 127 in the unclamping direction to disengage clamp heads 126, 127 and plug 122 such that plug 122 may be uncoupled from socket 124.

In examples, actuator 156 is configured to cause translation of clamp head 126 substantially concurrently (e.g., concurrently or nearly concurrently to the extent permitted by manufacturing tolerances) with causing translation of clamp head 127. In other examples, actuator 156 is configured to cause clamp head 126 to mechanically engage plug 122 prior to or following the mechanical engagement of clamp head 127 and plug 122. Actuator 156 may comprise one or more actuating devices configured to translate clamp heads 126, 127. For example, actuator 156 may include a first actuating device configured to cause translation of clamp head 126 and a second actuating device configured to cause translation of clamp head 127. Actuator 156 may include any number of actuating devices configured to cause translation of any number of clamp heads.

Connector 102 includes a control circuit 160 configured to provide electrical power to actuator 156. Control circuit 160 is configured to provide the electrical power to cause actuator 156 to translate clamp heads 126, 127. Control circuit 160 may include a power supply 162 configured to provide electrical power to control circuit 160. In examples, control circuit 160 includes circuitry 164 electrically connected to power supply 162. Circuitry 164 may be configured to receive electrical power from power supply 162 and provide the electrical power to actuator 156. In examples, circuitry 164 may include components configured as a current source configured to generate an output current using electrical power from power supply 162, with circuitry 164 configured to provide the output current to actuator 156 to provide electrical power to actuator 156. In examples, circuitry 164 may include components configured as a voltage source configured to generate an output voltage using electrical power from power supply 162, with circuitry 164 configured to apply the output voltage to actuator 156 to provide electrical power to actuator 156. Power supply 162 may be substantially dedicated to control circuit 160, or may also provide power to other components and/or systems, such as other components and/or systems of connector 102 and/or medical machine 104.

Plug 122 is configured to actuate control circuit 160 to cause control circuit 160 to provide the electrical power to actuator 156, such that actuator 156 translates clamp heads 126, 127 when plug 122 mechanically couples with socket 124. In some examples, plug 122 is configured to actuate a switch 166 of control circuit 160 when plug 122 mechanically mates with socket 124; such actuation of switch 166 causes control circuit 160 to provide the electrical power to actuator 156. Switch 166 may be configured to cause control circuit 160 to provide the electrical power to actuator 156 when switch 166 is actuated (e.g., in a closed position). Switch 166 may be any type of switch configured to actuate when plug 122 mechanically couples with socket 124, including a microswitch (e.g., a miniature snap-action switch), an electromechanical switch, a mechanical switch, a reed switches, a limit switch, or another type of switch configured to detect a proximity of plug 122 to socket 124. Switch 166 may be configured to detect the proximity of plug 122 to socket 124 in any manner, including contact with plug 122 or a component displaced by plug 122, a potentiometer position sensor, a linear variable differential transformer/voltage displacement (LVDT) transducer, a hall-effect magnetic sensor, a mechanical counter, a cam, an actuating arm, and the like.

In examples, socket 124 includes a pin 168 configured to actuate (e.g., close) switch 166 when pin 168 translates (e.g., in the direction D1). In some examples, pin 168 is a sliding pin configured to slidably translate (e.g., in direction D1) to actuate switch 166. In examples, plug 122 includes a skirt 170 extending from plug body 128, with skirt 170 configured to contact and translate sliding pin 168 when plug 122 mechanically mates with socket 124. As illustrated in FIG. 3, skirt 170 may cause pin 168 to translate and act to close switch 166, such that control circuit 160 provides electrical power to actuator 156, causing actuator 156 to translate clamp heads 126, 127 and mechanically engage plug body 128. For example, skirt 170 may be configured such that, when plug 122 translates in the direction D1 to mechanically mate with socket 124, skirt 170 contacts and causes a translation of pin 168 in the direction D1, causing pin 168 to actuate switch 166. In examples, pin 168 is mechanically supported by socket body 130 and configured to slidably translate relative to a portion of socket body 130.

In examples, switch 166 may be configured to de-actuate (e.g., open) when plug 122 is mechanically uncoupled from socket 124. For example, switch 166 may include an elastic element configured to compress and/or deform when skirt 170 translates pin 168 to actuate switch 166 and cause actuator 156 to translate clamp heads 126, 127. In examples, switch 166 includes an elastic cantilever configured to elastically deform when switch 166 actuates. For example, the elastic cantilever may be resiliently biased to place switch 166 in a de-actuated condition. Pin 168 may be configured to exert a force on the elastic cantilever to overcome the resilient biasing and place switch 166 in an actuated position. The elastic cantilever may be configured such that switch 166 de-actuates when plug 122 is mechanically uncoupled from socket 124 (e.g., when pin 168 ceases exerting the force). Clamp heads 126, 127 may be configured to generate a force on plug 122 sufficient to maintain the elastic element in a compressed and/or deformed condition. In some examples, switch 166 is a proximity switch configured to de-actuate and cause control circuit 160 to cease providing electrical power to actuator 156 when plug 122 is displaced from socket 124. Switch 166 may be configured to detect the displacement of plug 122 from socket 124 in any manner, contact with a component displaced by plug 122, a potentiometer position sensor, a linear variable differential transformer/voltage displacement (LVDT) transducer, a hall-effect magnetic sensor, a mechanical counter, a cam, an actuating arm, and the like.

In some examples, pin 168 includes a pin elastic element configured to compress and/or deform when skirt 170 translates pin 168. The pin elastic element may be configured to expand to exert a force on pin 168 which tends to separate pin 168 and switch 166, such that when skirt 170 is not in contact with pin 168 (e.g., when plug 122 is uncoupled with socket 124), the elastic element translates pin 168 in a direction away from switch 166, such that pin 168 may substantially re-set into an initial position when skirt 170 is not in contact with pin 168. Clamp heads 126, 127 may be configured to generate a force on plug 122 sufficient to maintain the pin elastic element in a compressed and/or deformed condition.

In examples, connector 102 includes an output device 172 configured to provide an output to a patient or other user when plug 122 mechanically mates with socket 124. This output may provide a positive indication to the user that a container (e.g., container 106) is properly connected to medical machine 104. The output provided by the output device 172 may be, for example, a light, a sound, a haptic output, or some other output discernable by the patient or other user. In examples, output device 172 is configured to provide the output when control circuit 160 is energized (e.g., when switch 166 is actuated by plug 122). In some examples, circuitry 164 is configured to detect when control circuit 160 is energized and cause output device 172 to provide the output. Circuitry 164 may cause output device 172 to provide the output. Output device 172 may be any device and include any circuitry configured to provide an output discernable by the patient or other user. In some examples, output device 172 is mechanically supported by housing 105 of medical machine 104. In other examples, output device 172 is an external device such as a smart phone, tablet, or other processing device configured to receive a communication from circuitry 164 via, for example, communication link 174.

In examples, output device 172 and/or control circuit 160 (e.g., circuitry 164) may be configured to provide an output to a control components and/or circuitry within medical machine 104 (FIG. 1) when plug 122 mechanically mates with socket 124. The control components and/or circuitry may be configured to use the output to control an operation of medical machine 104. For example, the control components and/or circuitry may use the output to determine if a medical treatment cycle enabled by medical machine 104 may commence and/or continue, e.g., based on whether the output from output device 172 indicates container 106 is properly fluidically connected to fluid line 110 of machine 104.

In examples, connector 102 includes an input device 176 configured to cause actuator 156 to translate clamp heads 126, 127 in the unclamping direction opposite the clamping direction to cause clamp heads 126, 127 to disengage from plug 122. Control circuit 160 may be configured to cause actuator 156 to translate clamp heads 126, 127 in the unclamping direction based on a signal from input device 176 received via, for example, communication link 178. Input device 176 may be configured to cause control circuit 160 to cause actuator 156 to translate clamp heads 126, 127 in the unclamping direction. Input device 176 may be configured to receive a user input and provide the user input to control circuit 160. In examples, circuitry 164 is configured to receive the user input from input device 176 and cause actuator 156 to translate clamp heads 126, 127 in the unclamping direction. Input device 176 may be any device (e.g., a button, switch, touchscreen, or the like) and include any circuitry configured to receive and input from a patient or other user or other processing circuitry. In some examples, input device 176 is mechanically supported by housing 105 of medical machine 104. In some examples, input device 176 is an external device such as a smart phone, tablet, or other processing device configured to transmit a communication to control circuit 160 (e.g., circuitry 164) via, for example, communication link 174.

In some examples, medical machine 104 includes a plurality of sockets such as socket 124 and socket 121 (FIG. 1). Connector 102 may be configured such that plug 122 is configured to mechanically mate with only one or more specific sockets mechanically supported by medical machine 104. For example, connector 102 may be configured to allow plug 122 to mechanically mate with socket 124 while substantially limiting and/or preventing plug 122 from mechanically mating with a different socket, such as socket 121 (FIG. 1). Limiting the sockets with which plug 122 may mechanically mate may limit and/or avoid misconnection of container 106 to a machine line mechanically supported by a socket other than socket 124.

In examples, and referring to FIG. 6, plug 122 (e.g., plug body 128) defines an outer cross-sectional dimension C1 (e.g., a diameter) and socket well 148 defines an inner cross-sectional dimension C2 (e.g., a diameter). Plug 122 may be configured such that outer dimension C1 allows plug 122 to insert into socket well 148 having inner dimension C2 when plug 122 mechanically mates with socket 124. For example, plug 122 may be configured such that outer dimension C1 allows plug 122 to insert within socket well 148 and cause plug seat 139 to mechanically engage socket seat 141 when plug 122 mechanically couples with socket 124.

Medical machine 104 may be configured such that a different socket such as socket 121 (FIG. 1) defines an inner cross-sectional dimension substantially preventing plug 122 from mechanically coupling with socket 121 or otherwise indicating to a user that the connection between plug 122 and socket 121 is improper. For example, the inner dimension of socket 121 may be less than outer dimension C1 of plug 122, such that plug 122 is substantially prevented from inserting into socket 121. As another example, plug 122 may fit in socket 121, but the outer dimension of plug 122 may be smaller or a different shape than socket 121 such that it is clear to a user that plug 122 is not intended to fit within socket 121. Outer dimension C1 may be a diameter defined by plug 122 and inner dimension C2 may be a diameter defined by socket 124.

In some examples, clamp heads 126, 127 defines an inner cross-sectional dimension C3. The inner dimension C3 may extend between clamp heads of connector 102, such as clamp head 126 and clamp head 127. In examples, inner dimension C3 extends from a clamp head 127 to a socket wall such as socket wall 149. Plug 122 may be configured such that outer dimension C1 enables plug 122 to insert into socket well 148 when clamp heads 126, 127 defines inner dimension C3, such that plug 122 may mechanically couple with socket 124. Clamp heads 126, 127 may be configured to define inner dimension C3 such that plug seat 139 mechanically engages socket seat 141 when plug 122 mechanically couples with socket 124. In some examples, medical machine 104 is configured such that a different socket such as socket 121 (FIG. 1) includes one or more clamp heads defining an inner cross-sectional dimension substantially preventing plug 122 from mechanically coupling with socket 121. For example, the inner dimension defined by clamp heads of socket 121 may be less than outer dimension C1 of plug 122, such that plug seat 139 is substantially prevented from mechanically engaging socket seat 141.

In examples, plug channel 132 defines an inner cross-sectional dimension C4 and socket 124 is configured to mechanically support a second conduit 110 defining an outer dimension C5. Plug channel 132 may be configured such that inner dimension C4 enables second conduit end 154 of second conduit 110 having outer dimension C5 to insert through plug outlet 136 and into plug channel 132 when plug 122 mechanically couples with socket 124 (as indicated in FIG. 3 and FIG. 5). In examples, plug channel 132 is configured such that inner dimension C4 causes plug channel 132 to establish a sliding fit with second conduit 110 mechanically engaged by socket 124 when plug 122 mechanically couples with socket 124.

In some examples, to help a user align plug 122 with the intended socket, medical machine 104 may be configured such that a different socket such as socket 121 (FIG. 1) is configured to support a machine line defining a different outer cross-sectional dimension less than or greater than C4, such that plug channel 132 is substantially prevented from mechanically mating with socket 121. For example, socket 121 may be configured to mechanically engage a machine line having an outer cross-sectional dimension greater than inner dimension C4 of plug channel 132, such that plug channel 132 is substantially prevented from receiving the machine line via plug outlet 136. As another example, the outer cross-sectional dimension of the machine line may be less than inner dimension C4 of plug channel 132, such that plug channel 132 is substantially prevented from establishing a sliding fit with the machine line. Inner dimension C4 may be a diameter defined by plug channel 132 and outer diameter dimension C5 may be a diameter defined by second conduit 110.

Plug 122 can also include one or more features configured to help a user align plug 122 with the proper socket 134. For example, plug 122 may define a stop 180 configured to protrude into plug channel 132. Stop 180 may be configured to contact second conduit end 154 when plug channel 132 receives second conduit 110 via plug outlet 136. Plug 122 may be configured such that stop 180 contacts second conduit end 154 substantially when plug seat 139 defined by plug 122 contacts socket seat 141 defined by socket 124. In some examples, plug 122 is configured to limit and/or prevent the mechanical coupling of plug 122 with another socket defined by medical machine 104, such as socket 121 (FIG. 1). For example, plug 122 may define stop 180 such that stop 180 is configured to contact a conduit end of a machine line mechanically engaged with socket 121 (which is not intended to receive plug 122) and prevent skirt 170 from actuating a switch configured to cause translation of a clamp head associated with socket 121. Hence, plug 122 may define stop 180 such that plug 122 is prevented from causing movement of a pin (similar to pin 168 but associated with socket 121) to prevent the delivery of power to the actuator associated with socket 121, such that the clamp head associated with socket 121 is prevented from translating to mechanically engage plug 122. In some examples, medical machine 104 may be configured to define individual sockets such as socket 124 and socket 121 such that only a specifically configured plug may cause a clamp head associated with an individual socket to mechanically engage the specifically configured plug.

As discussed above, in addition to or instead of the physical shape and/or size of plug 122 and socket 124 (e.g., stop 180), connector 102 can include one or more other features to help a user align plug 122 with the proper socket 124. For example, connector 102 can include visible indicia defined by one or more plugs and matching a respective socket to help a user align a plug with the proper socket.

Control circuit 160 and/or circuitry 164, as well as other control circuitry described herein, can comprise any suitable arrangement of hardware, software, firmware, or any combination thereof, to perform the techniques attributed to connector 102 herein. For example, control circuit 160 and/or circuitry 164 may include any one or more microprocessors, digital signal processors (DSPs), application specific integrated circuits (ASICs), field programmable gate arrays (FPGAs), or any other equivalent integrated or discrete logic circuitry, as well as any combinations of such components.

Communication links 174, 178, as well as other communication links described herein, may be hard-line and/or wireless communications links. In some examples, communication links 174, 178 may comprise some portion of control circuit 160 and/or circuitry 164. Communication links 174, 178 may comprise a wired connection, a wireless Internet connection, a direct wireless connection such as wireless LAN, Bluetooth™, Wi-Fi™, and/or an infrared connection. Communication links 174, 178 may utilize any wireless or remote communication protocol.

Figure 7:
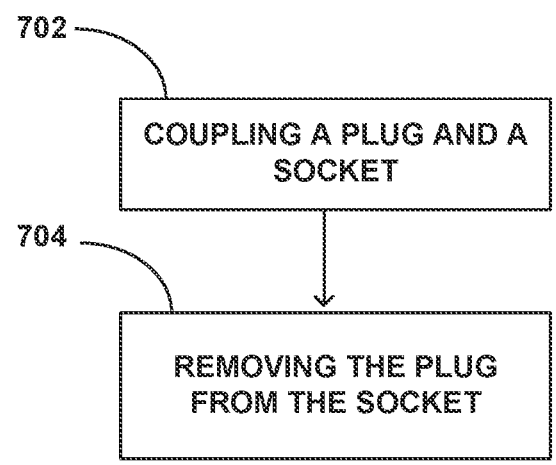
FIG. 7 is a flow diagram of an example technique of using a connector.

An example technique for connecting a container with medical machine 104 is illustrated in FIG. 7. Although the technique is described mainly with reference to connector 102 of FIGS. 1-6, the technique may be applied to other connectors and in other examples.

The technique includes mechanically mating plug 122 and socket 124 (702). In an example, one of plug 122 or socket 124 defines a protuberance and the other of plug 122 or socket 124 defines a cavity, and the cavity receives the protuberance when plug 122 mechanically couples with plug 122. In examples, plug seat 139 of plug 122 contacts socket seat 141 of socket 124 when plug 122 mechanically couples with socket 124. Plug 122 may define a protuberance configured to insert into socket well 148 defined by socket 124. Plug body 128 may contact socket body 130 when plug 122 mechanically couples with socket 124. In examples, plug seat 139 contacts socket seat 141 when plug 122 mechanically couples with socket 124. In examples, plug 122 is configured to mechanically couple with socket 124 when plug 122 is translated in the first direction D1 toward socket 124.

As discussed above, plug 122 is configured to cause control circuit 160 to provide electrical power to control circuit 160 when plug 122 mechanically couples with socket 124. Control circuit 160 may be configured to provide the electrical power to actuator 156, which is configured to translate clamp heads 126, 127 in response to receiving electrical power. In examples, plug 122 actuates switch 166 of control circuit 160 when plug 122 mechanically couples with socket 124 to cause control circuit 160 to provide the electrical power. Switch 166 may be configured to detect a proximity of plug 122 to socket 124 in any manner. In examples, plug 122 translates a pin 168 configured to actuate switch 166 when plug 122 mechanically mates with socket 124. In examples, plug 122 includes skirt 170 extending from plug body 128. Skirt 170 may be configured to contact and translate sliding pin 168 when plug 122 mechanically mates with socket 124. In examples, pin 168 is mechanically supported by socket body 130 and configured to slidably translate relative to a portion of socket body 130. Control circuit 160 is configured to cause output device 172 to provide an output to a patient or another user when plug 122 mechanically mates with socket 124.

Clamp heads 126, 127 is configured to mechanically engage plug 122 when actuator 156 translates clamp heads 126, 127. Clamp heads 126, 127 may be configured to minimize movements of plug 122 which might tend to cause an uncoupling of plug 122 and socket 124 when clamp heads 126, 127 mechanically engages plug 122. In examples, plug 122 mechanically couples with socket 124 when plug 122 translates in first direction D1, and clamp head 126 mechanically engages plug 122 to resist translation of plug 122 in second direction D2 opposite the first direction D1. In some examples, plug 22 inserts into socket well 148 defined by socket 124 when plug 122 mechanically couples with socket 124, and clamp heads 126, 127 substantially retains plug 122 within socket well 148 when clamp heads 126, 127 mechanically engages plug 122.

In examples, clamp heads 126, 127 establishes a frictional contact with plug body 128 when clamp heads 126, 127 mechanically engages plug body 128. Clamp heads 126, 127 may be configured such that the force exerted by clamp heads 126, 127 and the frictional contact between clamp heads 126, 127 and plug body 128 produces a frictional force on plug body 128 tending to resist movement of plug 122 relative to socket 124. For example, when plug 122 experiences a force in the direction D2, the frictional force may exert a force on the plug in the direction D1 to limit movement of plug 122. In some examples, one of clamp heads 126, 127 or plug body 128 defines a protrusion and the other of clamp heads 126, 127 or plug body 128 defines a recess, and the protrusion inserts into the recess when clamp heads 126, 127 mechanically engages plug 122. For example, plug body 128 may define a plug recess configured to receive clamp head 126. The protrusion and recess may be configured such that, when the protrusion is inserted in the recess, movement of plug 122 relative to socket 124 causes the protrusion and the recess to generate an action-reaction force pair limiting the relative movement.

In examples, clamp head 126 exerts a first force on plug 122 when clamp head 126 mechanically engages plug 122 and clamp head 127 exerts a second force on plug 122 opposing the first force when clamp head 127 mechanically engages plug 122. In some examples, clamp head 126 and clamp head 127 substantially surround plug 122 (e.g., surround an outer perimeter defined by plug body 128) when clamp head 126 and the clamp head 127 mechanically engage plug 122. Clamp head 126 and/or clamp head 127 may engage and/or substantially surround plug body 128 around any arc angle and/or portion of an outer perimeter defined by plug body 128. Connector 102 may include any number of clamp heads configured to mechanically engage plug 122 when plug 122 mechanically couples with socket 124.

In examples, clamp heads 126, 127 translates in a direction toward plug body 128 when plug 122 mechanically couples with socket 124. Clamp heads 126, 127 may translate in a direction from socket wall 149 toward plug body 128 when plug body 128 is inserted in socket well 148. Clamp heads 126, 127 may displace from a position adjacent socket wall 149 and toward plug body 128. In examples, clamp heads 126, 127 translates from the position adjacent socket wall 149 toward socket axis L to mechanically engage plug 122. In some examples, clamp heads 126, 127 displaces from socket wall in a direction substantially perpendicular to the direction D1 and/or socket axis L.

Plug 122 may form a connection between first conduit 108 mechanically engaged with plug inlet 134 and second conduit 110 mechanically supported by socket 124 when plug 122 mechanically mates with socket 124. In examples, plug channel 132 is configured to receive second conduit 110 via plug outlet 136 when plug 122 mechanically mates with socket 124. Plug 122 may include a stop 180 protruding into plug channel 132 and configured to contact second conduit end 154 when plug channel 132 receives second conduit 110. In examples, plug body 128 is configured to contact socket seat 141 of socket 124 when plug 122 mechanically mates with socket 124. Plug 122 may be configured such that stop 180 contacts second conduit end 154 when plug body 128 contacts socket seat 141. In examples, seat 164 comprises compressible material 143 (e.g., an O-ring or other compressible material), and plug body 128 contacts compressible material 143 when plug body 128 contacts socket seat 141. In examples, instead of or in addition to compressible material 143, plug body 128 contacts sealing system 145 to form a substantially fluidically sealed contact with second fluid conduit 110 when plug body 128 mechanically engages second fluid conduit 110.

The technique of FIG. 7 includes removing plug 122 from the socket 124 (704). Control circuit 160 may cause actuator 156 to translate the clamp head an unclamping direction opposite the clamping direction to cause clamp heads 126, 127 to disengage from plug 122. In examples, an input device 176 is configured to cause actuator 156 to translate clamp heads 126, 127 in the unclamping direction. Input device 176 may receive a user input from a patient or other user. Control circuit 160 may cause actuator 156 to translate clamp heads 126, 127 in the unclamping direction in response to the user input such that, for example, the patient or another user may translate plug 122 away from socket 124 to remove plug 122 from socket 124. Connector 102 may cause actuator 156 to translate clamp heads 126, 127 in the unclamping direction based on a signal received via, for example, communication link 178.

The present disclosure includes the following examples.

Example 1: A connector comprising: a plug defining a fluid channel extending between a plug inlet defined by the plug and a plug outlet defined by the plug, wherein the plug inlet is configured to mechanically engage a first conduit; a socket including a clamp head, wherein the socket is configured to mechanically engage a second conduit, and wherein the plug is configured to mechanically couple with the socket to fluidly couple the first conduit and the second conduit; an actuator configured to translate the clamp head to cause the clamp head to mechanically engage the plug when the actuator receives electrical power; and a control circuit configured to provide the electrical power to the actuator, wherein the plug is configured to cause the control circuit to provide the electrical power to the actuator when the plug mechanically couples with the socket, and wherein the clamp head is configured to help sustain the mechanical coupling of the plug and the socket when the clamp head mechanically engages the plug.

Example 2: The connector of example 1, wherein the plug is configured to mechanically couple with the socket when the plug translates in a first direction, and wherein the clamp head is configured to mechanically engage the plug to resist translation of the plug in a second direction opposite the first direction.

Example 3: The connector of example 1 or example 2, wherein the socket defines a socket body and the plug defines a plug body, wherein the plug body is configured to mechanically couple with the socket body, and wherein the actuator is configured to translate the clamp head relative to the socket body to cause the clamp head to mechanically engage the plug.

Example 4: The connector of any of examples 1-3, wherein the actuator is configured to cause the clamp head to exert a force on the plug when the clamp head mechanically engages the plug.

Example 5: The connector of any of examples 1-4, wherein the clamp head includes a first clamp head and the connector further comprises a second clamp head configured to mechanically engage the plug when the plug mechanically couples with the socket, wherein the actuator is configured to translate the second clamp head to cause the second clamp head to mechanically engage the plug, wherein the first clamp is configured to exert a first force on the plug when the first clamp head mechanically engages the plug and the second clamp is configured to exert a second force on the plug when the second clamp head mechanically engages the plug, and wherein the first force opposes the second force.

Example 6: The connector of any of examples 1-5, wherein the plug includes a plug body defining a recess, and wherein the clamp head is configured to insert into the recess when the clamp head mechanically engages the plug.

Example 7: The connector of any of examples 1-6, wherein the plug includes a plug body defining the fluid channel, and wherein the clamp head is configured to mechanically engage the plug body on a perimeter of the plug body.

Example 8: The connector of any of examples 1-7, wherein the socket is configured to fluidly couple the plug inlet and the second conduit when the clamp head mechanically engages the plug and the socket mechanically engages the second conduit.

Example 9: The connector of any of examples 1-8, wherein the socket includes a socket body defining a socket well, and wherein the plug is configured to insert into the socket well when the plug mechanically couples with the socket.

Example 10: The connector of example 9, wherein the clamp head is configured to mechanically engage a portion of the plug inserted within the socket well when the clamp head mechanically engages the plug.

Example 11: The connector of any of examples 1-10, wherein the control circuit includes a switch configured to cause the control circuit to provide the electrical power to the actuator, and wherein the plug is configured to actuate the switch when plug mechanically couples with the socket.

Example 12: The connector of example 11, wherein the socket includes a sliding pin configured to translate and actuate the switch, wherein the plug is configured to cause translation of the sliding pin to actuate the switch when plug mechanically couples with the socket.

Example 13: The connector of any of examples 1-12, wherein the control circuit is configured to transmit a signal to an output device when the control circuit provides the electrical power to the actuator.

Example 14: The connector of any of examples 1-13, wherein the actuator is configured to translate the clamp head in a clamping direction to cause the clamp head to mechanically engage the plug, and wherein the actuator is configured to translate the clamp head in an unclamping direction opposite the clamping direction to cause the clamp head to disengage from the plug.

Example 15: The connector of example 14, further comprising an input device configured to receive a user input and provide the user input to the control circuit, wherein the control circuit is configured to cause the actuator to translate the clamp head in the unclamping direction in response to the user input.

Example 16: A medical system comprising: the connector of any of examples 1-15; tubing defining the first conduit; and a dialysis machine comprising the second conduit.

Example 17: A connector comprising: a plug defining a fluid channel extending between a plug inlet defined by the plug and a plug outlet defined by the plug, wherein the plug inlet is configured to mechanically engage a first conduit; a socket including a first clamp head and a second clamp head, wherein the socket is configured to mechanically engage a second conduit, and wherein the plug is configured to mechanically couple with the socket to fluidly couple the first conduit and the second conduit, wherein the first clamp head is configured to exert a first force on the plug when the plug mechanically couples with the socket, wherein the second clamp head is configured to exert a second force on the plug when the plug mechanically couples with the socket, wherein the second force opposes the first force, and wherein the first clamp head is configured to exert the first force and the second clamp head is configured to exert the second force to help sustain the mechanical coupling of the plug and the socket; an actuator configured to receive electrical power, wherein the actuator is configured to translate the first clamp head to cause the first clamp head to exert the first force on the plug and configured to translate the second clamp head to exert the second force on the plug when the actuator receives the electrical power; and a control circuit configured to provide the electrical power to the actuator, wherein the plug is configured to cause the control circuit to provide the electrical power to the actuator when the plug mechanically couples with the socket.

Example 18: The connector of examples 17, wherein the control circuit is configured to transmit a signal to an output device when the control circuit provides the electrical power to the actuator.

Example 19: A method, comprising: mechanically coupling a plug and a socket, wherein the plug defines a plug inlet, a plug outlet, and a fluid channel extending between the plug inlet and the plug outlet, wherein the plug inlet is configured to mechanically engage a first conduit, and wherein the socket is configured to mechanically engage a second conduit, wherein when the plug mechanically couples with the socket, a control circuit provides electrical power to an actuator configured to translate a clamp head to mechanically engage the plug to help sustain the mechanical coupling of the plug and the socket; and, subsequently, decoupling the plug and the socket.

Example 20: The method of example 19, further comprising: fluidically connecting a container to a dialysis machine, wherein fluidically connecting the container to the dialysis machine comprises mechanically coupling the plug and the socket, wherein the plug is fluidically connected to the container and the socket is fluidically coupled to a fluid line of the dialysis machine.

Various examples of the disclosure have been described. Any combination of the described systems, operations, or functions is contemplated. These and other examples are within the scope of the following claims.

What is claimed is:

1. A connector comprising:
   a plug defining a fluid channel extending between a plug inlet defined by the plug and a plug outlet defined by the plug, wherein the plug inlet is configured to mechanically engage a first conduit;
   a socket including a clamp head, wherein the socket is configured to mechanically engage a second conduit, and wherein the plug is configured to mechanically couple with the socket to fluidly couple the first conduit and the second conduit;
   an actuator configured to translate the clamp head to cause the clamp head to mechanically engage the plug when the actuator receives electrical power; and
   a control circuit configured to provide the electrical power to the actuator,
   wherein the plug is configured to cause the control circuit to provide the electrical power to the actuator when the plug mechanically couples with the socket, and
   wherein the clamp head is configured to help sustain the mechanical coupling of the plug and the socket when the clamp head mechanically engages the plug.

2. The connector of claim 1, wherein the plug is configured to mechanically couple with the socket when the plug translates in a first direction, and wherein the clamp head is configured to mechanically engage the plug to resist translation of the plug in a second direction opposite the first direction.

3. The connector of claim 1, wherein the socket defines a socket body and the plug defines a plug body, wherein the plug body is configured to mechanically couple with the socket body, and wherein the actuator is configured to translate the clamp head relative to the socket body to cause the clamp head to mechanically engage the plug.

4. The connector of claim 1, wherein the actuator is configured to cause the clamp head to exert a force on the plug when the clamp head mechanically engages the plug.

5. The connector of claim 1,
wherein the clamp head includes a first clamp head and the connector further comprises a second clamp head configured to mechanically engage the plug when the plug mechanically couples with the socket,
wherein the actuator is configured to translate the second clamp head to cause the second clamp head to mechanically engage the plug,
wherein the first clamp is configured to exert a first force on the plug when the first clamp head mechanically engages the plug and the second clamp is configured to exert a second force on the plug when the second clamp head mechanically engages the plug, and
wherein the first force opposes the second force.

6. The connector of claim 1, wherein the plug includes a plug body defining a recess, and wherein the clamp head is configured to insert into the recess when the clamp head mechanically engages the plug.

7. The connector of claim 1, wherein the plug includes a plug body defining the fluid channel, and wherein the clamp head is configured to mechanically engage the plug body on a perimeter of the plug body.

8. The connector of claim 1, wherein the socket is configured to fluidly couple the plug inlet and the second conduit when the clamp head mechanically engages the plug and the socket mechanically engages the second conduit.

9. The connector of claim 1, wherein the socket includes a socket body defining a socket well, and wherein the plug is configured to insert into the socket well when the plug mechanically couples with the socket.

10. The connector of claim 9, wherein the clamp head is configured to mechanically engage a portion of the plug inserted within the socket well when the clamp head mechanically engages the plug.

11. The connector of claim 1, wherein the control circuit includes a switch configured to cause the control circuit to provide the electrical power to the actuator, and wherein the plug is configured to actuate the switch when plug mechanically couples with the socket.

12. The connector of claim 11, wherein the socket includes a sliding pin configured to translate and actuate the switch, wherein the plug is configured to cause translation of the sliding pin to actuate the switch when the plug mechanically couples with the socket.

13. The connector of claim 1, wherein the control circuit is configured to transmit a signal to an output device when the control circuit provides the electrical power to the actuator.

14. The connector of claim 1, wherein the actuator is configured to translate the clamp head in a clamping direction to cause the clamp head to mechanically engage the plug, and wherein the actuator is configured to translate the clamp head in an unclamping direction opposite the clamping direction to cause the clamp head to disengage from the plug.

15. The connector of claim 14, further comprising an input device configured to receive a user input and provide the user input to the control circuit, wherein the control circuit is configured to cause the actuator to translate the clamp head in the unclamping direction in response to the user input.

16. A medical system comprising:
the connector of claim 1;
tubing defining the first conduit; and
a dialysis machine comprising the second conduit.

17. The connector of claim 1, wherein the control circuit is configured to transmit a signal to an output device when the control circuit provides the electrical power to the actuator.

18. A connector comprising:
a plug defining a fluid channel extending between a plug inlet defined by the plug and a plug outlet defined by the plug, wherein the plug inlet is configured to mechanically engage a first conduit;
a socket including a first clamp head and a second clamp head, wherein the socket is configured to mechanically engage a second conduit, and wherein the plug is configured to mechanically couple with the socket to fluidly couple the first conduit and the second conduit,
wherein the first clamp head is configured to exert a first force on the plug when the plug mechanically couples with the socket,
wherein the second clamp head is configured to exert a second force on the plug when the plug mechanically couples with the socket, wherein the second force opposes the first force, and
wherein the first clamp head is configured to exert the first force and the second clamp head is configured to exert the second force to help sustain the mechanical coupling of the plug and the socket;
an actuator configured to receive electrical power, wherein the actuator is configured to translate the first clamp head to cause the first clamp head to exert the first force on the plug and configured to translate the second clamp head to exert the second force on the plug when the actuator receives the electrical power; and
a control circuit configured to provide the electrical power to the actuator, wherein the plug is configured to cause the control circuit to provide the electrical power to the actuator when the plug mechanically couples with the socket.

19. A method, comprising:
mechanically coupling a plug and a socket, wherein the plug defines a plug inlet, a plug outlet, and a fluid channel extending between the plug inlet and the plug outlet, wherein the plug inlet is configured to mechanically engage a first conduit, and wherein the socket is configured to mechanically engage a second conduit, wherein when the plug mechanically couples with the socket, a control circuit provides electrical power to an actuator configured to translate a clamp head of the socket to mechanically engage the plug to help sustain the mechanical coupling of the plug and the socket; and, subsequently,
decoupling the plug and the socket.

20. The method of claim 19, further comprising:
fluidically connecting a container to a dialysis machine, wherein fluidically connecting the container to the dialysis machine comprises mechanically coupling the plug and the socket, wherein the plug is fluidically connected to the container and the socket is fluidically coupled to a fluid line of the dialysis machine.

* * * * *